(12) United States Patent
Archer

(10) Patent No.: US 9,155,891 B2
(45) Date of Patent: Oct. 13, 2015

(54) CURRENT MANAGEMENT SYSTEM FOR A STIMULATION OUTPUT STAGE OF AN IMPLANTABLE NEUROSTIMULATION SYSTEM

(75) Inventor: Stephen T. Archer, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 1378 days.

(21) Appl. No.: 12/886,279

(22) Filed: Sep. 20, 2010

(65) Prior Publication Data

US 2012/0071950 A1    Mar. 22, 2012

(51) Int. Cl.
*A61N 1/36* (2006.01)

(52) U.S. Cl.
CPC ........ *A61N 1/36125* (2013.01); *A61N 1/36157* (2013.01)

(58) Field of Classification Search
CPC .............. A61N 1/025; A61N 1/36125; A61N 1/36128; A61N 1/36146; A61N 1/36157; A61N 1/36153; A61N 1/3615
USPC ...................................... 607/2, 45–46, 59, 66
See application file for complete search history.

(56) References Cited

U.S. PATENT DOCUMENTS

| | | | |
|---|---|---|---|
| 5,154,172 A | 10/1992 | Terry, Jr. et al. | |
| 5,222,494 A | 6/1993 | Baker, Jr. | |
| 6,016,449 A | 1/2000 | Fischell et al. | |
| 6,516,227 B1 | 2/2003 | Meadows et al. | |
| 6,662,053 B2 | 12/2003 | Borkan | |
| 6,690,974 B2 | 2/2004 | Archer et al. | |
| 6,810,285 B2 | 10/2004 | Pless et al. | |
| 7,146,222 B2 | 12/2006 | Boling | |
| 7,174,213 B2 | 2/2007 | Pless | |
| 7,444,181 B2 * | 10/2008 | Shi et al. | 607/2 |
| 7,570,999 B2 | 8/2009 | Libbus et al. | |
| 7,596,414 B2 | 9/2009 | Whitehurst et al. | |
| 2007/0100399 A1 | 5/2007 | Parramon et al. | |
| 2007/0142863 A1 | 6/2007 | Bradley | |
| 2008/0027504 A1 | 1/2008 | Bedenbaugh | |
| 2009/0118787 A1 | 5/2009 | Moffitt et al. | |
| 2009/0125079 A1 | 5/2009 | Armstrong et al. | |
| 2009/0157155 A1 | 6/2009 | Bradley | |
| 2009/0240302 A1 | 9/2009 | Woods et al. | |
| 2010/0023070 A1 | 1/2010 | Moffitt et al. | |
| 2010/0023097 A1 | 1/2010 | Peterson et al. | |
| 2010/0106219 A1 | 4/2010 | Torgerson et al. | |

(Continued)

*Primary Examiner* — Paula J Stice
(74) *Attorney, Agent, or Firm* — Arent Fox LLP

(57) ABSTRACT

A current management system for use in the stimulation output stage of a neurostimulation system can be programmed to steer different amounts of current through different stimulation electrodes to vary how strongly the tissue adjacent each electrode is stimulated during a particular programmed stimulation episode. An stimulation electrode drive circuit associated with each electrode that is available for stimulation allows independent control of the flow of current through that electrode. A reference electrode is provided in the circuit to source or sink current as necessary to balance the currents going into and out of the patient, so that no stimulation electrode is required to serve that purpose. More specifically, by configuring the circuit to maintain a constant potential at the reference electrode (e.g., a potential that is approximately half way between a top and bottom voltage rail), the reference electrode will source or sink currents as necessary to cause the net current flow into the patient to be equal to the net current flowing out of the patient, thus satisfying Kirchhoff's current law.

6 Claims, 9 Drawing Sheets

(56) References Cited

U.S. PATENT DOCUMENTS

| | | |
|---|---|---|
| 2010/0331923 A1 | 12/2010 | Peterson |
| 2011/0093041 A1 | 4/2011 | Straka et al. |
| 2011/0093042 A1* | 4/2011 | Torgerson et al. ............... 607/59 |
| 2012/0046712 A1 | 2/2012 | Woods et al. |
| 2012/0130448 A1 | 5/2012 | Woods et al. |
| 2013/0013025 A1 | 1/2013 | Parramon et al. |
| 2013/0218248 A1 | 8/2013 | Moffitt et al. |

* cited by examiner

CURRENT MANAGEMENT SYSTEM FOR A STIMULATION OUTPUT STAGE OF AN IMPLANTABLE NEUROSTIMULATION SYSTEM

GOVERNMENT CONTRACT

The U.S. Government has a paid-up license in this invention and the right in limited circumstances to require the patent owner to license others on reasonable terms as provided for by the terms of the Department of Commerce, National Institutes of Standards and Technology, Cooperative Agreement No. 70NANB7H7001.

FIELD

The disclosed embodiments relate to current control systems, and more particularly to current control systems in implantable neurostimulation systems that can deliver electrical stimulation as a form of therapy to a patient through one or more electrodes.

BACKGROUND

Neurostimulation systems, and increasingly implantable neurostimulation systems, are used to treat various neurological diseases and other neurological disorders, such as epilepsy, movement disorders (e.g., Parkinson's disease) and chronic pain. Research is ongoing concerning use of implantable neurostimulation systems to treat psychological disorders (e.g., depression), headaches and Alzheimer's disease and to facilitate stroke recovery.

A typical neurostimulation system comprises a stimulation source, such as a pulse generator, and a stimulation output (or therapy output) stage through which a form of stimulation (e.g., electric current or voltage) can be delivered to target neural tissue. The output stage is in communication with a plurality of electrodes that are disposed in or near the target brain tissue. For example, a brain lead can be used to connect multiple electrodes located on a distal end of the lead through conductors to a proximal end of the lead which then can be connected to the neurostimulator. The electrode-bearing leads may be designed so that the electrodes are intended to be placed on a surface of the brain (cortical strip electrodes on a cortical strip lead) or within the brain (deep brain electrodes on a deep brain or depth lead).

The stimulation to be delivered to the patient is typically programmable. For example, a neurostimulator may be loaded with a set of programmed instructions that cause it to initiate a stimulation episode according to a particular schedule or in response to some predetermined physiological condition or conditions or a neurological event or events. Various parameters related to the stimulation episodes also may be predetermined by programming, for example, whether the stimulation episode consists of pulsatile or non-pulsatile stimulation, and, if pulsatile, how many pulses in a burst, how many bursts within the episode, and the amplitude, frequency or pulse-to-pulse intervals within a burst all may be programmable. In addition, the electrodes among the electrodes available for stimulation through which a stimulation episode is delivered can be preselected by programming. For instance, there may be four electrodes on the distal end of a deep brain lead, all of which are available for use in a stimulation episode, and the neurostimulation system may be programmable to deliver stimulation for a given stimulation episode in a bipolar fashion from the most proximal electrode on the lead to the next most proximal electrode on the lead, or between the first three most proximal electrodes and the most distal electrode.

As will be appreciated by those with skill in the art, there may be circumstances in which it would be desirable to be able to program a neurostimulation system so that different amounts of current can be delivered through different stimulation electrodes at a given instant, for example, to deliver stronger stimulation to the location adjacent one of the electrodes than the stimulation delivered at the location(s) adjacent the other(s). Thus, what is needed is a device and method associated with a neurostimulation system for independently controlling the current that is delivered through each of a plurality of electrodes available for stimulation.

SUMMARY

A current management system for the stimulation output stage of a neurostimulation system is disclosed in which it is possible to independently control the current flow through each of a plurality of electrodes in a set of stimulation electrodes so that, for example, the strength of the stimulation near a given one of the electrodes in the set can be reliably estimated and the current delivered can be steered among several different stimulation electrodes.

In one variation, the neurostimulation system is implantable in a human patient and the current management system provides programmed instructions from which digital control and timing signals are derived that determine what function which stimulation electrode will have at what time during a stimulation episode; the functions for each stimulation electrode are implemented by a stimulation electrode drive circuit for each electrode and including causing the stimulation electrode to source current into the patient, sink current out of the patient, present a high impedance (e.g., turn the electrode "off"), and provide a short circuit to ground. The reservoir voltage for each electrode drive circuit allows it to cause its associated stimulation electrode to source or sink current within limits (e.g., the limits of a top and bottom voltage rail). The total amount of current being sourced or sunk through the stimulation electrodes at any given time in the stimulation electrode is balanced by an equal amount of current sunk or sourced through a reference electrode, by maintaining the reference electrode at a constant voltage.

In some variations, a bias circuit is provided, for example, for each stimulation electrode drive circuit, to convert the programmed instructions in the form of digital control and timing signals into a digital enable signal and an analog signal containing information to establish the reference current for a given sourcing or sinking function.

In some variations, the voltages in the current management system are above and below ground, for example, a top voltage rail is above ground, a bottom voltage rail is below ground, and the reference electrode is maintained at around ground potential. In some variations, all of the voltages in the current management system are at or above ground, for example, a bottom rail voltage is around ground, and the reference electrode drive circuit sets the reference electrode voltage at a midrail voltage between ground and a top rail voltage.

The voltages used by the current management system may be derived from a power source in a neurostimulator, such a primary cell battery or a rechargeable battery. The voltages may be increased by boost converter circuits (e.g., voltages of up to +16 V may be derived from a 3 V battery).

In other variations, a "TILT" signal is generated whenever a programmed amount of current cannot be sourced or sunk through a stimulation electrode because the limits defined by the top and bottom voltage rails are exceeded.

In still other variations, the voltages in the current management system are automatically adjustable within predetermined not-to-exceed values whenever a programmed amount of current cannot be sourced or sunk through a stimulation electrode because the limits defined by the top and bottom voltage rails are exceeded, the adjustment being such to allow the programmed amount of current to be delivered so long as the programmed amount of current can be delivered within the not-to-exceed values.

Also described herein is a method for steering the amount of current to be sourced or sunk to a patient through each of a plurality of stimulation electrodes under the control of a neurostimulator in a neurostimulation system. A stimulation electrode drive circuit is provided for each stimulation electrode and is configurable to cause the associated stimulation electrode to perform one of four functions at any given time period in a stimulation episode, namely, sourcing current into the patient, sinking current out of the patient, presenting a high impedance, or providing a short circuit to ground. Programmed instructions are provided in the form of digital control and timing signals to each stimulation electrode drive circuit to cause the associated stimulation electrode to perform one or more of the four functions at selected time periods during the stimulation episode. A voltage reservoir for the stimulation electrode drive circuits is provided for when the stimulation electrode drive circuits are programmed to source or sink currents. A reference electrode drive circuit is provided that maintains a housing of the neurostimulator at a constant reference voltage during the stimulation episode, which causes the reference electrode to source or sink an amount of current equal to the total amount of current being sunk or sourced by the stimulation electrodes at each selected time period. This allows the current sourced or sunk through any one stimulation electrode to be independent of the amount of current being sourced or sunk through any other stimulation electrode at any given time period in the stimulation episode.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

DETAILED DESCRIPTION

Figure 1:
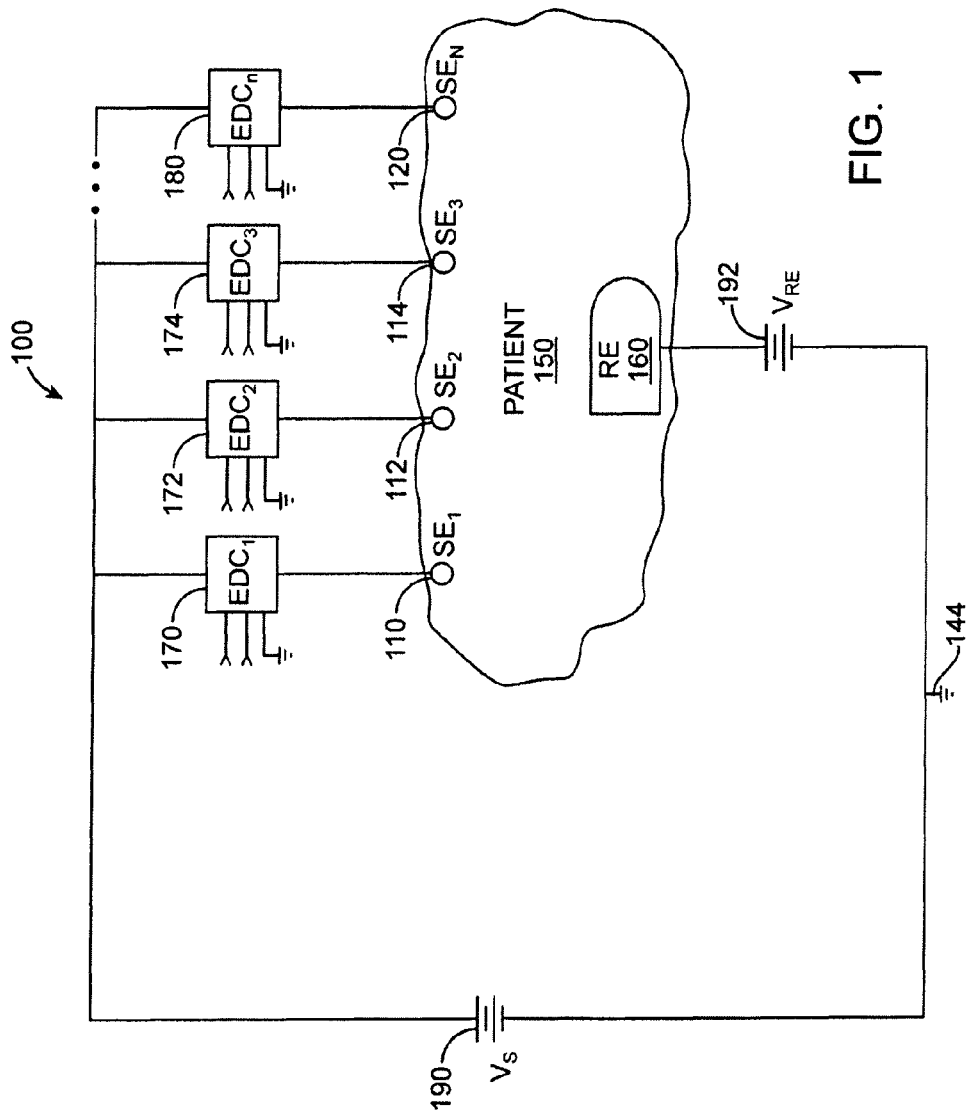
FIG. 1 is a schematic diagram illustrating a current management system for a stimulation output stage of a neurostimulation system.

Various embodiments are now described with reference to the figures where like reference numbers indicate identical or functionally similar elements. Also in the figures, the left most digits of each reference number corresponds to the figure in which the reference number is first used.

Reference in the specification to "some embodiments" or "some variations" means that a particular feature, structure, or characteristic described in connection with these embodiments or variations is included in at least one embodiment or at least one variation of the invention. The references of the phrase "in some embodiments" or "in some variations" in various places in the specification are not necessarily all referring to the same embodiment or variation.

All publications, patents, and patent applications cited herein are hereby incorporated by reference in their entirety for all purposes to the same extent as if each individual publication, patent, or patent application were specifically and individually indicated to be so incorporated by reference.

As used herein, the term "stimulation episode" refers to any instance in which electrical stimulation is delivered to a patient through one or more electrodes configured for that purpose. A stimulation episode may be characterized by one or more parameters that determine how long the episode will last, of what sort of stimulation the episode will be comprised (e.g., pulsatile stimulation, non-pulsatile stimulation, pulsatile or nonpulsatile stimulation with a direct current component, etc.), how strong the stimulation delivered will be at any given point in the episode (e.g., amplitude of the stimulation, duration of the stimulation); whether the stimulation will be delivered in bursts within a stimulation episode and, if so, the number, frequency and shape (morphology) of pulses within a burst, the delay between pulses within a burst or between bursts or between transitions from positive-going pulses to negative-going pulses, etc. A stimulation episode may also be defined with reference to which or how many electrodes in a set of electrodes will be used in delivering it. Although the term "stimulation episode" is used herein almost exclusively with reference to electrical current stimulation, the term should be understood to encompass within its scope alternative forms of stimulation where such meaning is not precluded in a particular context.

A current management system implemented in the stimulation (or therapy) output stage of an implantable neurostimulation system is described in which each of several electrodes available for use in a stimulation episode is provided with its own stimulation electrode drive circuit, which can be configured to source or sink current (with respect to the patient) based on digital control and timing signals that are derived from programmed instructions conveyed through or by another system or by another subsystem of the neurostimulation system, and a further reference electrode is provided to be maintained at a constant reference voltage, by sinking or sourcing current to balance what is happening at the stimulation electrodes.

FIG. 1 is a schematic diagram illustrating a current management system 100 for a neurostimulation system including stimulation electrodes $SE_1$ 110, $SE_2$ 112, $SE_3$ 114 through $SE_N$ 120 each connectable through its own stimulation electrode drive circuit, $EDC_1$ 170, $EDC_2$ 172, $EDC_3$ 174 through $EDC_N$ 180 to a supply voltage $V_S$ 190. Throughout operation of the current management system, the reference electrode RE 160 is configured to maintain a constant voltage $V_{RE}$ 192 by source and sinking currents through a patient 150 to balance any currents sunk or sourced through the stimulation electrodes $SE_1$ 110, $SE_2$ 112, $SE_3$ 114 through $SE_N$ 120, as is explained more fully below. The voltage $V_{RE}$ to be maintained at the reference electrode RE 160 might be half the supply voltage $V_S$ 190. (In other variations, the current management system may be configured to maintain the reference electrode RE at ground potential, where the electrode drive circuits are powered by voltages around ground, e.g., by a voltage $V_P$ that is above ground, and a voltage $V_N$ equal to $V_P$ but below ground, such as $V_P$=+8 V and $V_N$=−8 V.) The programmed instructions determine whether and when any given switch to connect a stimulation electrode to a patient is closed during all or a part of a stimulation episode. If a stimulation electrode is used in a stimulation episode, the stimulation electrode drive circuit associated with that stimulation electrode will configure the stimulation electrode to source or sink current at the appropriate times according to the parameters of the stimulation episode.

The action of each stimulation electrode drive circuit that is programmed to be active during a stimulation episode ("active electrode drive circuit") will be controlled by at least one control signal and at least one clock signal. More specifically, the control signal(s) together with the timing signal(s) will determine, during a given stimulation episode, whether a particular stimulation electrode is sourcing or sinking current during discrete time periods or segments of the stimulation episode and, if so, what will be the amplitude of the current. Alternatively, the control signal(s) together with the timing signal(s) can be used to cause an electrode to look like an open circuit (high impedance), for example, to "turn it off" during a segment or during a portion of a segment, such as when transitioning between sourcing and sinking functions (similar to a "break-before-make" condition that might be used with control of a switch). In still other circumstances, the control and timing signals can be used to cause the electrode to look like a short circuit (low impedance), for example, to allow any charge that has built up at the electrode-to-tissue interface to discharge. Thus, the control and timing signal(s) in operation with each stimulation electrode's electrode drive circuit can cause each stimulation electrode to have one of four possible functions during each segment of a stimulation episode, namely, a current source with a given amplitude, a current sink with a given amplitude, a high impedance, or a low impedance.

Figure 2:
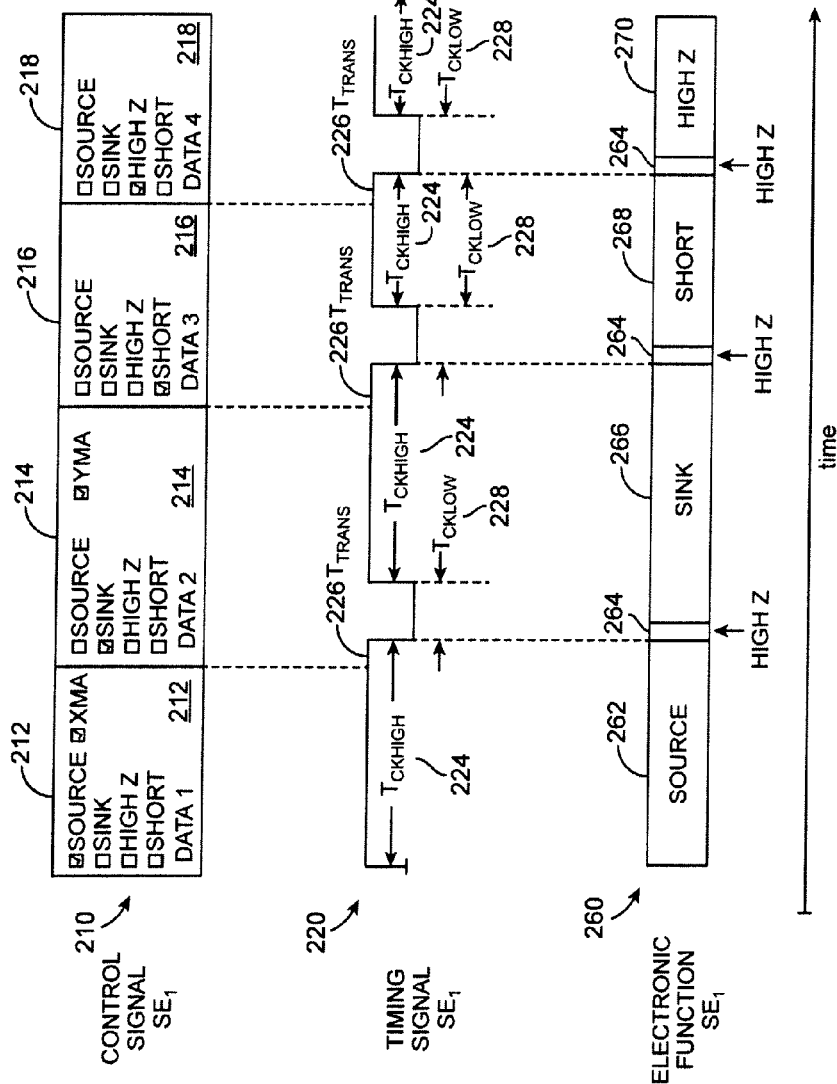
FIG. 2A is a graphical illustration of a control signal for a stimulation electrode.
FIG. 2B is a graphical illustration of a timing signal for a stimulation electrode.
FIG. 2C is a graphical illustration of the function of an electrode corresponding to the control signal and timing signal of FIGS. 2A and 2B.

FIGS. 2A-2C illustrate one example of an interaction between a control signal and a timing signal with respect to what is happening at one stimulation electrode $SE_1$ 110 (i.e., the function the electrode serves based on the control and timing signals. FIG. 2A is a representation of a control signal 210 with time on the x-axis for a stimulation electrode $SE_1$ 110. Packets of information, as might be delivered over a bus, are indicated as "DATA1" 212, "DATA2" 214, "DATA3" 216 and "DATA4" 218. Each packet of information can specify the function the electrode is to perform, as well as certain parameters corresponding to a predetermined stimulation episode. For example, if DATA1 212 contains information that will set the function of the stimulation electrode $SE_1$ 110 to perform as a current source (i.e., to deliver current to the patient), the DATA1 212 packet may also specify the strength of the current (e.g., current amplitude in mA). A timing signal 220, such as derived from a clock, is shown in FIG. 2B, and the function of the electrode $SE_1$ 110 relative to the timing signal 220 is shown in FIG. 2C. Thus, when the timing signal 220 is high during the time period $T_{CKHIGH}$ 224, the stimulation electrode $SE_1$ 110 will carry out the function specified in the packet DATA1 212, e.g., to source current into the patient at an amplitude of X mA. The current sourcing function of the stimulation electrode $SE_1$ 110 during the first clock high period $T_{CKHIGH}$ 224 is shown in FIG. 2C as the rectangle 262.

Optionally, it may be desirable for the function of the stimulation electrode to transition briefly to a high impedance state after one function is performed and the next function begins (similar to a "break-before-make" design as might be used in a switching circuit). Such a short high impedance transition can be appreciated with reference to FIGS. 2B and 2C. More specifically, whenever the clock signal transitions from a high state to a low state at $T_{TRANS}$ 226, the stimulation electrode $SE_1$ 110 is configured to have a high impedance (i.e., look like an open circuit) 264 for a short period of time relative to the time periods in which the stimulation electrode $SE_1$ 110 is performing one of its functions. In one variation, an appropriate duration for this brief "High Z" state between different electrode functions may be 200 nS. In practice, the brief high impedance state between transistions of an electrode from one function to another may be accomplished with the timing signals used to enable or disable the flow of current through an electrode. For example, the programming may be such it causes the flow of current through an electrode to start after a short delay (e.g., when a sourcing or sinking function for that electrode is enabled) but it causes the flow of current to stop without delay (e.g., when a sourcing or sinking function is disabled). This will put an electrode in a high impedance state during a transistion between functions in which current is programmed to flow through the electrode. The short High Z period may be implemented by adjusting the digital timing and/or control signals.

Referring still to FIGS. 2A-2C, after the short high impedance period 264, the presence of information packet DATA2 214 in the control signal 210 causes the stimulation electrode $SE_1$ 110 to change functions and perform as a current sink 266 (i.e., sinking current out of the patient). The amplitude, Y mA, of this current is specified in the packet DATA1 214. The stimulation electrode during the second transition $T_{TRANS}$ 226 shown in FIG. 2B will continue to sink Y mA of current as long as the timing signal 220 stays high (during the second time period $T_{CKHIGH}$ 224 in FIG. 2B). When the timing signal 220 again transitions to a low state (during the second transition $T_{TRANS}$ 226 shown in FIG. 2B), the stimulation electrode $SE_1$ 110 will be in a high impedance state 264 for a brief period before transitioning to the function specified in the next information packet in the control signal 210, namely, DATA3 216. DATA3 216 specifies a short circuit for the stimulation electrode function. Thus, following the third brief high impedance state 264 shown in FIG. 2C, the stimulation electrode $SE_1$ 110 will perform as a short circuit for so long as the timing signal remains high (i.e., the third time period $T_{CKHIGH}$ 224 in FIG. 2B. Finally, on the next transition of the timing signal 220 from high to low (during the third transition $T_{TRANS}$ 226 shown in FIG. 2B), and after the fourth brief high impedance state 264 shown in FIG. 2C, the stimulation electrode $SE_1$ 110 will remain in the high impedance state, since that is the function for electrode that is specified in the last information packet 218 of the control signal 210 shown in FIG. 2A. Thus, the stimulation electrode $SE_1$ 110 will look like a high impedance to the rest of the circuit, for so long as the timing signal 220 remains high (during the fourth time period $T_{CKHIGH}$ 224 in FIG. 2B). It will be apparent that a stimulation episode as realized at a given one of the stimulation electrodes may be controlled by different control signals that have more or less information regarding electrode function than is described in connection with FIGS. 2A-2C above. Similarly, it will be appreciated that a timing signal for a stimulation electrode can be provided with more or less complicated transitions may be used in connection with a given stimulation episode.

It will be apparent to one skilled in the art that if a single clock signal is used for all of the stimulation electrodes that are selected for a given stimulation episode, then the electrodes will change functions according to what is specified in each electrode's control signal at the same times. In other words, the electrodes will function synchronously with each other. Of course, each electrode nevertheless may be performing different functions at different times even when they share a single clock signal. For example, if three stimulation electrodes $SE_1$ 110, $SE_2$ 112, and $SE_3$ 114 are used to deliver stimulation in a given stimulation episode and each of the stimulation electrodes is associated with its own control signal 210 but with a common timing signal 220, the control signals may specify different functions for each of $SE_1$ 110, $SE_2$ 112, and $SE_3$ 114 even though function changes (to the extent any are specified in the control signals) will occur at the same time. For the first time period when the timing signal 220 is high ($T_{CKHIGH}$ 224), the first stimulation electrode $SE_1$ 110 might have the function of a current source at $X_1$ mA, the second stimulation electrode $SE_2$ 112 might have the function of looking like a high impedance, and the third stimulation electrode $SE_3$ 114 might have the function of a current source at $X_2$ mA. After the transition to the second time period stimulation electrode when the timing signal 220 is high ($T_{CKHIGH}$ 224), the first stimulation electrode $SE_1$ 110 might have the function of a current source at $X_3$ mA, the second stimulation electrode $SE_2$ 112 may continue to be high impedance, and the third stimulation electrode $SE_3$ 114 may change to a current sink at $Y_1$ mA. Alternatively, and with a shared timing signal 220, some of the stimulation electrodes may have a "break-before-make" high impedance state between transitions from one type of function (e.g., sourcing) to another (e.g., sinking) and some may not.

On the other hand, if the stimulation electrodes do not share a clock signal but rather each electrode is supplied with its own dedicated clock signal, it would be possible to cause each electrode to operate according to different phases within a stimulation episode, for example, one electrode could be switching between current sourcing and current sinking functions twice as fast as another electrode is switching between sourcing and sinking functions, or one electrode could remain shorted for half as long as another electrode remains high impedance, and so on and so forth. Indeed, it is envisioned that in some variations, multiple stimulation electrodes may be provided with the same control signal but different timing signals, so that different functions for different electrodes might be enabled at different times.

At any given instant during a stimulation episode, the reference electrode RE will try to source or sink current as necessary (i.e., based on how each stimulation electrode is functioning) to maintain the voltage $V_{RE}$ constant. For example, if, at a time $t_1$, the stimulation electrode drive circuits for the stimulation electrodes active for this stimulation episode try to deliver stimulation so that a net current of 3 mA will be sourced into the patient, the reference electrode will have to sink 3 mA from the patient. If there is not sufficient voltage difference between the reference electrode ($V_{RE}$) and the positive or negative supply voltage to allow this to happen, then the programmed current cannot be delivered. (In one variation, the condition where the programmed amount of current cannot be sourced or sunk due to insufficient reservoir voltage is called a "TILT" and is described more fully below). However, if there is sufficient voltage for the reference electrode to sink the 3 mA, the amount of current going into the patient will be balanced by the amount of current going out of the patient, thus satisfying Kirchhoff's current law for the circuit.

Thus, the presence of the reference electrode in the circuit allows each stimulation electrode to perform its functions independently of what is happening at every other stimulation electrode. When the stimulation electrodes are programmed to source current, this means that known amounts of current can be steered through different stimulation electrodes at desired times, thus providing the person who is programming the neurostimulation system (i.e., the programmer) with the ability to deliver stimulation of varying strengths to the locations in the patient adjacent each electrode.

Figure 3:
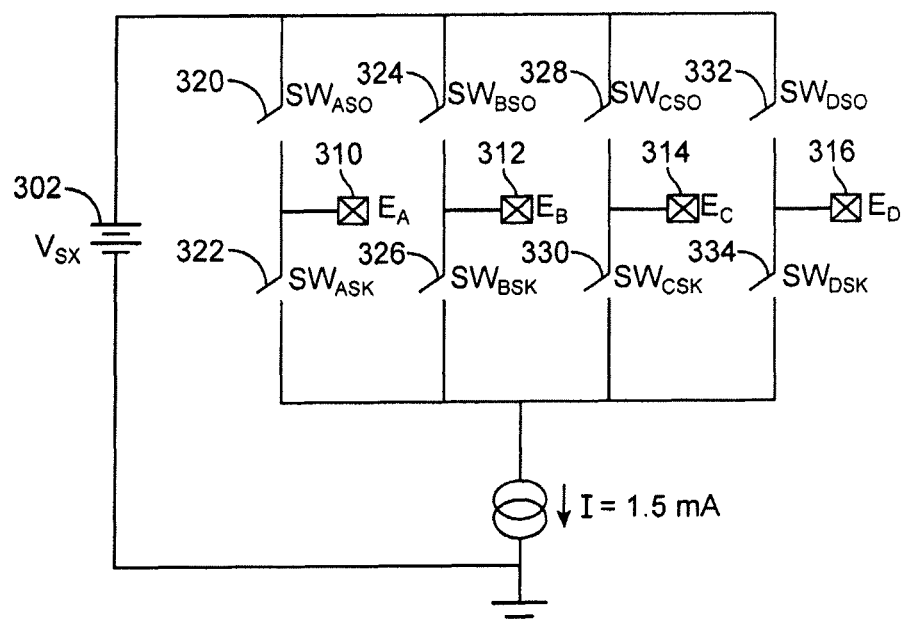
FIG. 3 is schematic diagram of a prior art stimulation output stage for a neurostimulator.

This is to be contrasted to the situation in which a single current source is used to drive a parallel combination of electrodes. In this situation, due to impedance mismatching among the parallel electrodes (and any lead(s) through which the electrodes are connected to the current generator), the amount of current passing through each electrode cannot be precisely controlled. FIG. 3 illustrates a stimulation output stage for a neurostimulation system when two or more electrodes are configured to source or sink current in parallel. In FIG. 3, there are four electrodes $E_A$ 310, $E_B$ 312, $E_C$ 314 and $E_D$ 316 adjacent the tissue of a patient (the patient is not represented in FIG. 3). The four electrodes are arranged in parallel in a circuit supplied by a voltage $V_{SX}$ 302. An electrode can be selected to source or sink current by the switches $SW_{ASO}$ 320, $SW_{ASK}$ 322, $SW_{BSO}$ 324, $SW_{ASK}$ 326, $SW_{CSO}$ 328, $SW_{CSK}$ 330, $SW_{DSO}$ 332, $SW_{DSK}$ 334. For example, the first electrode $E_A$ 310 can be enabled to source current into the patient by closing switch $SW_{ASO}$ 320 to connect the first electrode $E_A$ 310 to the voltage $V_{SX}$ 302, or to sink current out of the patient by closing $SW_{ASK}$ 322 to connect the first electrode $E_A$ 310 to ground. For a particular stimulation episode, the first electrode $E_A$ 310, the second electrode $E_B$ 312, and the third electrode $E_C$ 314 might be selected from among the electrodes available for stimulation. More particularly, the first and second electrodes $E_A$ 310 and $E_B$ 312 may be selected to source current into the patient, for example, because the programmer wants to stimulate the area adjacent those two electrodes, and the third electrode $E_C$ 314 may be selected as a return electrode, to sink the current sourced by the first and second electrodes out of the patient. To accomplish this, switch $SW_{ASO}$ 320 would be closed to source current through the first electrode $E_A$ 310, switch $SW_{BSO}$ 324 would be closed to source current through the second electrode $E_B$ 312 and switch $SW_{CSK}$ 330 would be closed to sink the current sourced by the first and second electrodes through the third electrode $E_C$ 314. The programmer might have in mind that, since the first and second electrodes $E_A$ 310 and $E_B$ 312 are connected in parallel, equal amounts of current will be sourced through each electrode. However, if the impedances of the first and second electrodes are not matched, then the programmer will not be in a position to know exactly how much of the total amount of current that is programmed to be sourced will be sourced through each of the first and second electrodes. For example, if the total amount of current that is programmed to be sourced is 1.5 mA, and the impedance of the first electrode $E_A$ 310 is half as much as the impedance of the second electrode $E_B$ 312, the first electrode will carry twice as much current as the second electrode, or the first electrode will carry 1.0 mA and the second electrode will carry 0.5 mA. (As will be appreciated by those with skill in the art, the programmer's decision of how strongly to stimulation through the electrodes selected for stimulation also will be informed, in part, by the charge density at the electrodes which is dependent on the electrode surface area.) In any event, and as a practical matter, the programmer will not know the exact impedances at the stimulation electrodes at any given moment in time, and the impedances will change with time, so the opposition to the current flowing through a given electrode as compared to other stimulation electrode cannot be predetermined or predicted for any particular stimulation episode.

Returning now to the instant current management system for a therapy output stage of a neurostimulation system, the reference electrode preferably is configured to have a surface area that is sufficient to keep whatever currents are flowing through it at a low enough charge density so that the functioning of the reference electrode is not a factor the programmer must take into consideration when determining the strength of the stimulation to be delivered at any given stimulation electrode at any given phase.

Figure 4:
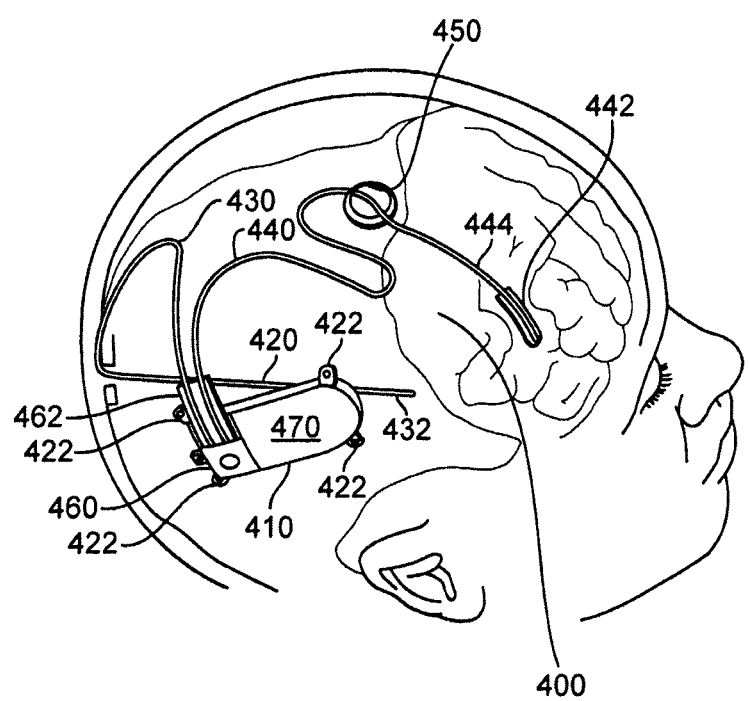
FIG. 4 is a perspective view of a neurostimulation system implanted in the head of a human patient.

With reference now to FIG. 4, a perspective view of one type of implantable neurostimulation system 400 is illustrated. The neurostimulator 410 is situated in a ferrule 420 that is seated in an opening formed in the patient's cranium (as by a craniotomy) and attached to the cranium with fasteners 422 using bone screws or the like. The electrodes available for use in a stimulation episode are located near the distal end of each of two brain leads 430, 440 (electrodes not shown in FIG. 4). Each of the leads 430, 440 is introduced to the patient's brain through a burr hole 450.

Two different types of brain leads are indicated in FIG. 4. Lead 430 is referred to as a depth lead or deep brain lead, because the ring electrodes (not shown) at the distal end 432 thereof are implanted in a patient's brain. Lead 440 is referred to as a cortical strip lead because the disc-shaped electrodes (not shown) disposed on a strip 442 on distal end 444 thereof are usually implanted adjacent a surface of the brain as opposed to in the brain, such as on a surface of the brain under the dura mater. Electrode-bearing deep brain leads and cortical strip leads are described, for example, in U.S. Pat. No. 7,146,222 to Boling for "Reinforced Sensing and Stimulation Leads and Use in Detection Systems," issued Dec. 5, 2006.

The proximal portions of each brain lead 430, 440 extend over the cranium and each brain lead is connected near the proximalmost portion thereof to a lead connector 460 attached to the neurostimulator 410. A strain relief 462 is provided at the point where the distal ends of the brain leads 430, 440 are connected to the lead connector 460. The lead connector 460 puts the electrodes at the end of each brain lead 430, 440 in operable communication with the systems and subsystems of the neurostimulator 410 (e.g., a programmable therapy subsystem associated with a pulse generator), which are contained with a housing or device case 470. (Neurostimulation systems, including the components and subsystems of the neurostimulator are described in, for example, U.S. Pat. No. 6,016,449 to Fischell et al. for "System for Treating Neurological Disorders," issued Jan. 18, 2000; and U.S. Pat. No. 6,810,285 to Pless et al. for "Seizure Sensing and Detection Using and Implantable Device," issued Oct. 26, 2004. U.S. Pat. No. 6,690,974 to Archer et al. for "Stimulation Signal Generator for an Implantable Device" issued Feb. 10, 2004 includes a description of an output stimulation stage for a neurostimulation system.)

The device case 470 and the ferrule 420, among other components of the neurostimulation system, are formed of a biocompatible metal, such as titanium, and thus constitute electrically conductive surfaces which can be used alone or together as a reference electrode RE 160. The conductive area of the device case typically is much larger than the conductive area of each of the stimulation electrodes, so the current density at the device case will be much lower than any current densities at a stimulation electrode-to-tissue interface. For example, in the neurostimulation system currently under investigation by NeuroPace, Inc. under the name "RNS SYSTEM," the surface area of the housing (or device case or "can") of the implantable neurostimulator is on the order of 30 cm². The RNS SYSTEM can be configured with either depth brain leads or cortical strip leads, and each electrode on either type of lead has a surface area on the order of 0.8 cm².

The independent control of the stimulation electrodes characteristic of the current management system 100 will be further described with reference to FIGS. 5-7.

Figure 5:
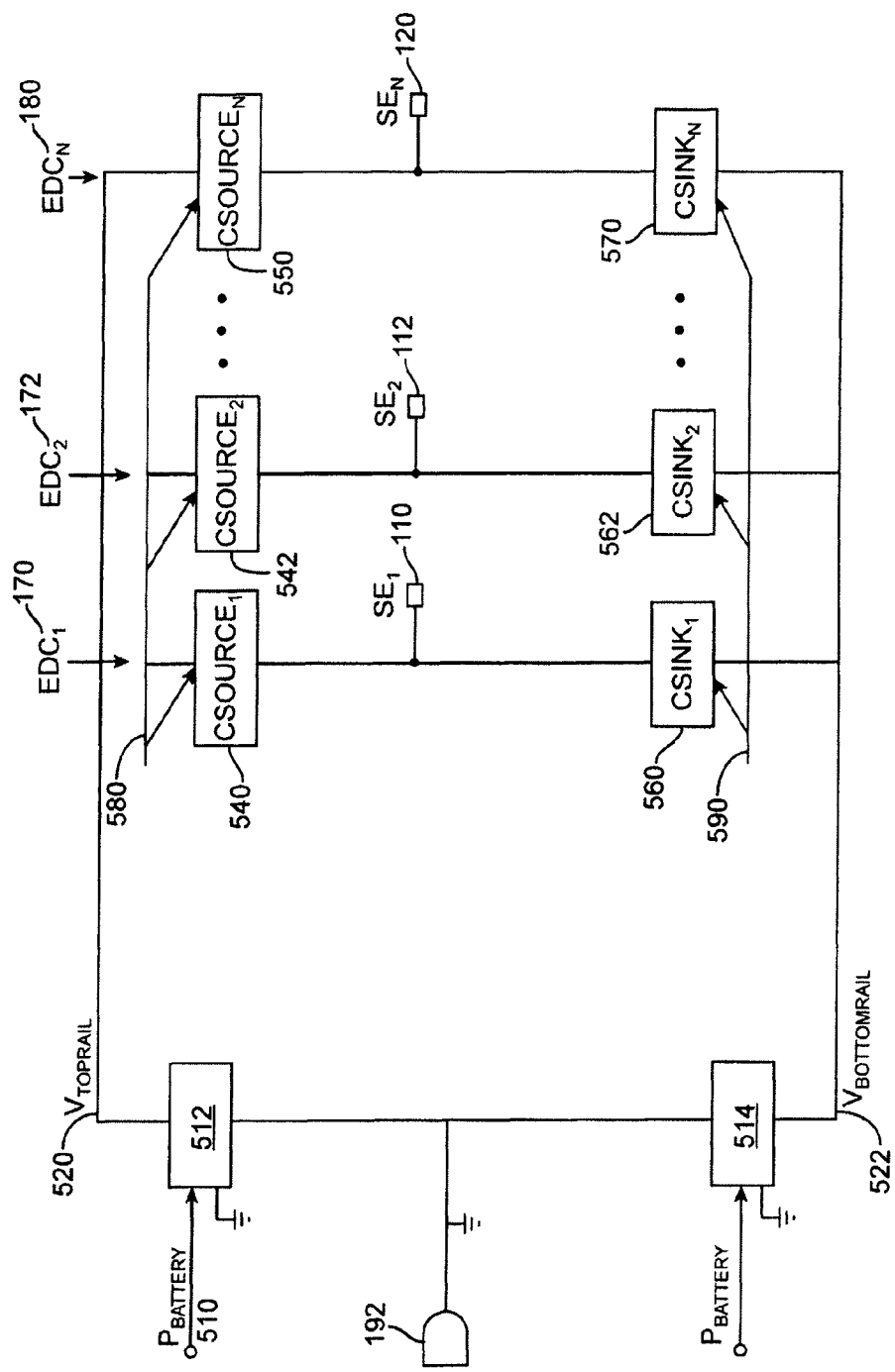
FIG. 5 is a schematic diagram illustrating some of the circuit elements for a current management system for a stimulation output stage of a neurostimulation system where the potential at which the reference electrode is maintained is at or near ground potential.

FIG. 5 illustrates stimulation electrode drive circuits $EDC_1$ 170, $EDC_2$ 172 through $EDC_N$ 180, operably associated with stimulation electrodes $SE_1$ 110, $SE_2$ 112 through $SE_N$ 120 and reference electrode RE 160. Power from a battery $P_{BATTERY}$ 510 (for example a primary cell (non-rechargeable) battery or a secondary (rechargeable) battery included as a power source in the implantable neurostimulator (see, e.g., the neurostimulator 410 of FIG. 4) is boosted with first and second boost converters 512, 514 to create the voltages between which the stimulation electrode drive circuits will operate. As will be appreciated by one skilled in the art, the boost converter is a DC-to-DC converter with an output voltage that is greater than the source voltage, which in one variation is from a voltage that is referenced to ground and derived from the positive pin of a battery with a voltage of approximately 3V. The first boost converter 512 is configured to create a top rail voltage $V_{TOPRAIL}$ 520 and the second boost converter 514, is configured to create a bottom rail voltage $V_{BOTTOMRAIL}$ 522. The voltages $V_{TOPRAIL}$ 520 and $V_{BOTTOMRAIL}$ 522 may be above and below ground potential, respectively, for example, in one variation, $V_{TOPRAIL}$ 520=$V_P$=+8.0 V and $V_{BOTTOMRAIL}$ 522=$V_N$=−0.8 V. In other variations, $V_{TOPRAIL}$ 520 may be above ground potential and $V_{BOTTOMRAIL}$ 522 may be at ground potential for example, where the technology used in implementing the circuit necessitates the use of voltages that are at or above ground. An example of a current management system using all voltages that are at ground potential or higher is described with references to FIG. 9.

With continued reference to FIG. 5, each of $V_{TOPRAIL}$ 520 and $V_{BOTTOMRAIL}$ 522 are adjustable between a maximum voltage (e.g., $V_{TOPRAIL}$ 520=+8 V, $V_{BOTTOMRAIL}$ 522=-8 V) to source or sink current through the stimulation electrodes $SE_1$ 110 through $SE_N$ 120 and RE 160. Each of the stimulation electrodes $SE_1$ 110, $SE_2$ 112 through $SE_N$ 120 is associated with its own stimulation electrode drive circuit $EDC_1$ 170, $EDC_2$ 172 through $EDC_N$ 180. Each stimulation electrode drive circuit has a current sourcing portion and a current sink portion, i.e., current source portion $CSOURCE_1$ 540 and current source portion $CSINK_{1560}$ of electrode drive circuit $EDC_1$ 170 are associated with stimulation electrode $SE_1$ 110, $CSOURCE_2$ 542 and current source portion $CSINK_2$ 562 of electrode drive circuit $EDC_2$ 172 are associated with stimulation electrode $SE_2$ 112, and so on, such that if there are N stimulation electrodes, $CSOURCE_N$ 550 and current source portion $CSINK_N$ 570 of electrode drive circuit $EDC_N$ 180 are associated with stimulation electrode $SE_N$ 120. The current source portions $CSOURCE_1$ 540, $CSOURCE_2$ 542 through $CSOURCE_N$ 550 have a first logic control 580 that is distinct from a second logic control 590 that is provided for $CSINK_1$ 560, $CSINK_2$ 562 through $CSINK_N$ 570 so that, for any given stimulation electrode $SE_1$ 110, $SE_2$ 112 through $SE_N$ 120 the current management system 100 cannot try to source and sink current through a stimulation electrode at the same time.

In this configuration, the current that any one stimulation electrode $SE_1$ 110, $SE_2$ 112 through $SE_N$ 120 is able to deliver is unaffected by the impedance at any of the other stimulation electrodes $SE_1$ 110, $SE_2$ 112 through $SE_N$ 120, provided that the voltages $V_{TOPRAIL}$ 520 and $V_{BOTTOMRAIL}$ 522 are sufficient to drive whatever amount of current the electrode is programmed to deliver. In other words, because each stimulation electrode is associated with an independent electrode drive circuit rather than having one current source/sink circuit associated with all of the electrodes, each electrode will source or sink the precise amount of current it is programmed to source or sink, regardless of what is happening at any other electrode. In order to maintain the voltage $V_{RE}$ at the reference electrode RE 160 constant, the reference electrode will sink or source current as necessary to keep the total amount of current balanced (i.e., so that the net current going into the patient is equal to the net current coming out of the patient at any given instant during a stimulation episode).

Of course, a programmed amount of current may not be deliverable through a given stimulation electrode when the product of the impedance at the electrode and the programmed current is greater the voltage available to supply the applicable current source or sink (e.g. the difference between one of the rail voltages $V_{TOPRAIL}$ 520 or $V_{BOTTOMRAIL}$ 522 and the reference electrode voltage $V_{RE}$ 192). This condition, where the stimulation reservoir voltage is insufficient to support the programmed stimulation current is called a "TILT." As will be discussed in more detail below, one variation of a current management system has features that allow the system to automatically adjust itself to increase the reservoir voltage so that the programmed current can be supported.

Figures 6A, 6B, 6C, 6D, 6E:
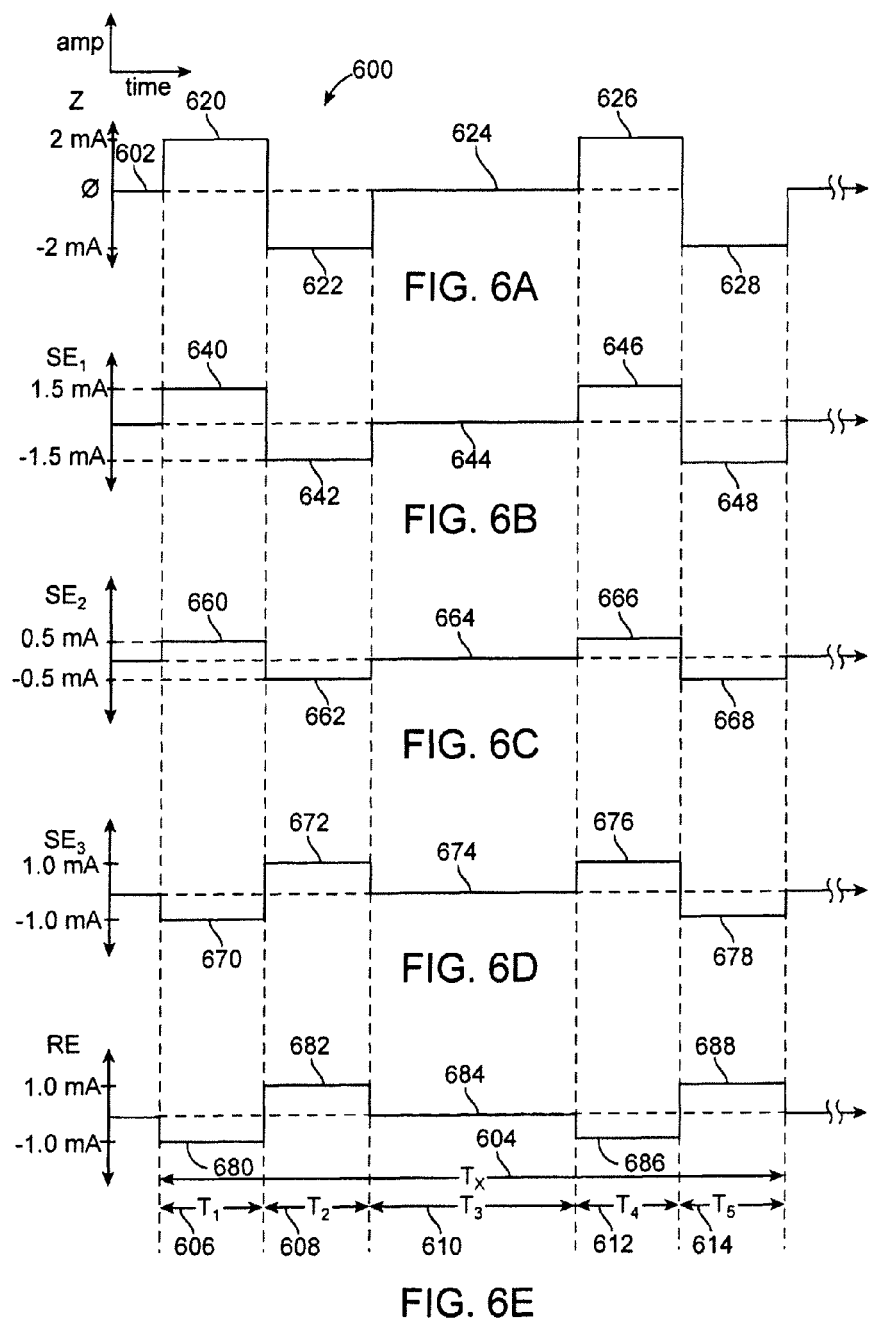
FIG. 6A is a graphical illustration of a stimulation episode that might be used with a current management system for a stimulation output stage of a neurostimulation system.
FIG. 6B is a graphical illustration of the current passing through a first stimulation electrode of a neurostimulation system during the stimulation episode of FIG. 6A.
FIG. 6C is a graphical illustration of the current passing through a second stimulation electrode of a neurostimulation system during the stimulation episode of FIG. 6A.
FIG. 6D is a graphical illustration of the current passing through a third stimulation electrode of a neurostimulation system during the stimulation episode of FIG. 6A.
FIG. 6E is a graphical illustration of the current passing through a reference electrode of a neurostimulation system during the stimulation episode of FIG. 6A.

An example of operation of the current management system will now be described with reference to FIG. 6A-6E, all of which represent time on the x-axis and current amplitude on the y-axis. A stimulation episode 600 is depicted in FIG. 6A, as a biphasic pulsatile waveform 602 formed from a series of biphasic pulses of equal amplitude (a pulse train comprising two instances the same positive and negative pulses (four pulses altogether) is shown in FIG. 6A) over the time period $T_X$ 604. One of the two positive/negative combination comprises a first pulse 620 with an amplitude of 2 mA lasting for a time $T_1$ 606 and a second pulse 622 with an equal and opposite amplitude of -2 mA lasting for a time $T_2$ 608. After a time $T_3$ 610 in which there is no current stimulation scheduled, i.e., the stimulation signal portion 624 of the stimulation episode 600 is intended to be inactive (i.e., zero), the second of the two positive/negative combinations comprises a third pulse 626 lasting for a time $T_4$ 612 and a fourth pulse 628 lasting for a time $T_5$ 614.

For this particular stimulation episode 600, a programmer has determined that it would be desirable to stimulate the area in the vicinity of the first stimulation electrode $SE_1$ 110 most strongly, with pulses having an amplitude of ±1.5 mA over the time period $T_X$ 604 (as shown in FIG. 6B), and to stimulate the area in the vicinity of the second stimulation electrode $SE_2$ 112 less strongly, with pulses having an amplitude of ±0.5 mA. A third stimulation electrode $SE_3$ 114 is configured as a return electrode (e.g., in a bipolar configuration with one or both of the first and second stimulation electrodes 110, 112). However, the third stimulation electrode $SE_3$ 114 is programmed to only source and sink current having an amplitude of ±1 mA over the time period $T_X$. So the reference electrode RE 160 is left with having to source and sink current having an amplitude of ±1 mA in order to balance the net current going into the patient (i.e., ±1.5 mA from the first stimulation electrode $SE_1$ 110 and ±0.5 mA from the second stimulation electrode $SE_2$ 112) with the net current returning through the patient to ground (i.e., the current being sunk by the patient, ±1.0 mA through the third stimulation electrode $SE_3$ 114 and ±1.0 mA through the reference electrode RE 160).

More specifically, and referring to FIGS. 6B and 6C, at $T_1$ 606, the stimulation electrode $SE_1$ 110 delivers a positive 1.5 mA pulse 640 to the patient (i.e., sources 1 mA) and the stimulation electrode $SE_2$ 112 delivers a positive 0.5 mA pulse 660 to the patient, totaling the +2 mA called for at $T_1$ in the stimulation episode 600. Also in the first time period at time $T_1$ 606, the stimulation electrode $SE_3$ 114 sinks 1.0 mA through the patient (indicated by the -1.0 mA pulse 670 in FIG. 6D). Referring to FIG. 6D, the reference electrode RE 160 sinks 1.0 mA (as represented by the -1.0 mA signal 680) at time $T_1$ 606, in order to keep the voltage at the reference electrode, $V_{RE}$ 192, constant. Referring to the same FIGS. 6A-6D, at time $T_2$ 608, the stimulation episode 600 calls for a -2.0 mA pulse 622, and the stimulation electrode $SE_1$ 110 and the stimulation electrode $SE_2$ 112 are programmed to sink a total of 2.0 mA (i.e., -1.5 mA through stimulation electrode $SE_1$ 110 at signal portion 642 and -0.5 mA through stimulation electrode $SE_2$ 112 at signal portion 662). But the third stimulation electrode $SE_3$ 114 is only programmed to source 1.0 mA at time $T_2$ 608 (see the third stimulation electrode signal portion 672), so the reference electrode RE 160 has to make up the difference and source another 1.0 mA at time $T_2$ 608 (see the reference electrode signal portion 682).

During the next period 624 in the stimulation episode 600 at time $T_3$ 610, all of the stimulation electrodes are effectively off (no current is flowing through any of them) (at time $T_3$ 610, see the signal portion 644 for the first stimulation electrode $SE_1$ 110 in FIG. 6B, the signal portion 664 for the stimulation electrode $SE_2$ 112 in FIG. 6C, and the signal portion 674 for the third stimulation electrode $SE_3$ 114 in FIG. 6C), so the reference electrode does not need to source or sink any current (at time $T_3$ 610, see the signal portion 684 for the reference electrode RE 160).

The second of the two sets of biphasic pulses occurs in the stimulation episode 600 at times $T_4$ 612 with the positive 2.0 mA pulse 626 and $T_5$ 614 with the negative 2.0 mA pulse 628. The operation of the three stimulation electrodes and the reference electrodes is repeated from the first and second time period $T_1$ 606 and $T_2$ 608 for the fourth and fifth time periods $T_4$ 612 and $T_5$ 614 based on the stimulation episode 600 and the stimulation electrode programming. That is, at time period $T_4$ 612, the stimulation electrode $SE_1$ 110 sources 1.5 mA (see the signal portion 646 in FIG. 6B), the stimulation electrode $SE_2$ 112 sources 0.5 mA (see the signal portion 666 in FIG. 6C), the stimulation electrode $SE_3$ 114 sinks 1.0 mA (see the signal portion 676 in FIG. 6D), and the reference electrode 160 sinks 1.0 mA (see the signal portion 686 in FIG. 6E) to maintain the voltage $V_{RE}$ 192 at the reference electrode constant. Then, at time period $T_5$ 614, the stimulation electrode $SE_1$ 110 sinks 1.5 mA (see the signal portion 648 in FIG. 6B), the stimulation electrode $SE_2$ 112 sinks 0.5 mA (see the signal portion 668 in FIG. 6C), the stimulation electrode $SE_3$ 114 sources 1.0 mA (see the signal portion 678 in FIG. 6D), and the reference electrode 160 sinks 1.0 mA (see the signal portion 688 in FIG. 6E).

The foregoing example is a relatively simple one (e.g., no break-before-make conditions are illustrated) and the three stimulation electrodes are all programmed to change function at the same times. It will be appreciated that the reference electrode RE 160 can continuously balance the current being sourced or sunk relative to the patient when the stimulation episodes and programming are far more complex, such as when different control signals for different stimulation electrodes are derived from a given stimulation episode, or the timing of when each stimulation electrode changes function is different for different ones of the stimulation electrodes within a given stimulation episode, or when there is more than one stimulation episode to be delivered through a given set of stimulation electrodes at the same time, etc.

Some additional examples include: (1) programming a first stimulation electrode $SE_1$ to source 1 mA and a second stimulation electrode $SE_2$ to source 1 mA during a first time $T_1$ of a stimulation episode, where no stimulation electrodes are programmed to sink current at time $T_1$: in this case, the reference electrode RE will sink 2 mA; (2) programming a first stimulation electrode $SE_1$ to source 1 mA, a second stimulation electrode $SE_2$ to source 1 mA, and a third stimulation electrode $SE_3$ to sink 1 mA during a first time $T_1$ of a stimulation episode, such that the reference electrode RE will sink 1 mA; (3) programming a first stimulation electrode $SE_1$ to source 1.5 mA for the first half of a first time period $T_1$ and to sink 0.5 mA for the second half of the first time period $T_1$, programming a second stimulation electrode $SE_2$ to sink 1.0 mA for all of the first time period $T_1$: in this case, the reference electrode will sink 0.5 mA for the first half of the first time period $T_1$ and will source 0.5 mA for the second half of the first time period $T_1$; and (4) programming each of three stimulation electrodes to source 2 mA and programming no stimulation electrode to sink any current, thus leaving the reference electrode to sink all 6 mA.

Figure 7:
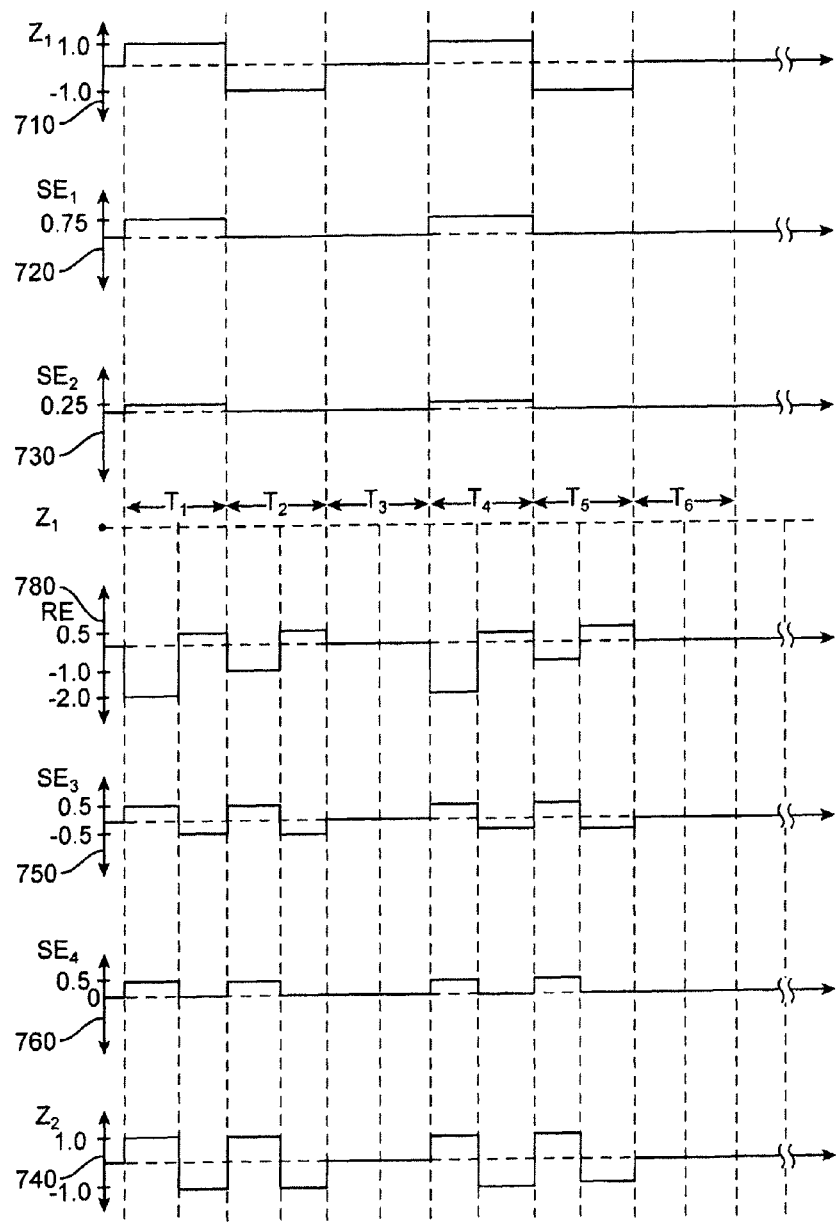
FIG. 7 is a graphical illustration the current passing through each of four stimulation electrodes and a reference electrode during two different stimulation episodes.

FIG. 7 illustrates the action at the reference electrode 160 in an example that is slightly more complex than the example illustrated in FIGS. 6A-6E. In FIG. 7, the graphs 710 and 720 correspond to the behavior of the first and second stimulation electrodes $SE_1$ 110 and $SE_2$ 112 programmed based on the parameters of a first stimulation episode, stimulation episode "$Z_1$," corresponding to the top graph 710 of FIG. 7. The graphs 750 and 760 correspond to the third and fourth stimulation electrodes $SE_3$ 114 and $SE_4$ 116 programmed based on the parameters of a second stimulation episode, stimulation episode "$Z_2$" corresponding to the bottom graph 740 of FIG. 7. The action at the reference electrode RE 160 corresponds to the middle graph 780 in FIG. 7. Both the first stimulation episode $Z_1$ and the second stimulation episode $Z_2$ are composed of sets of biphasic current pulses separated by an interval in which no current is being sourced or sunk (intervals $T_3$ and $T_6$ in FIG. 7). However, the pulses in the second stimulation episode $Z_2$ are delivered twice as fast as the pulses in the first stimulation episode $Z_1$.

Figure 8:
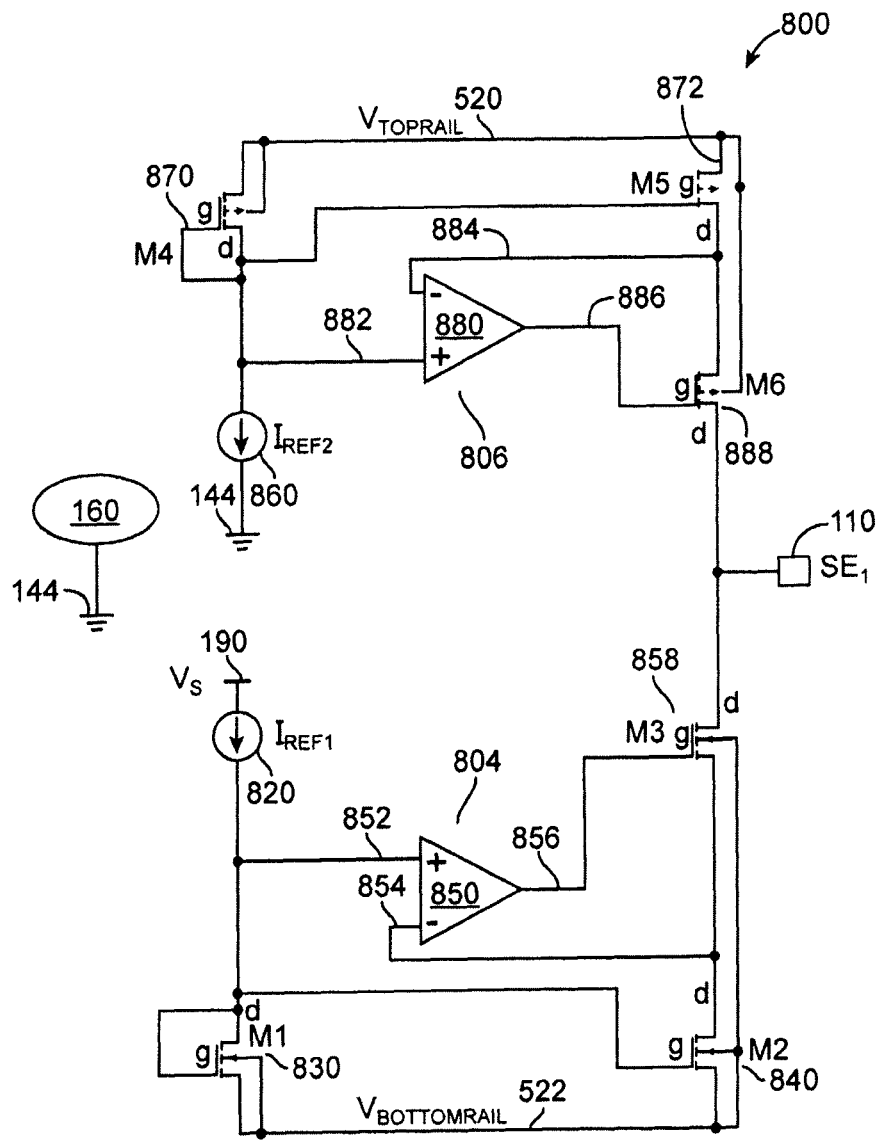
FIG. 8 is a schematic diagram of a stimulation electrode drive circuit of a current management system of a neurostimulation system where the potential at which the reference electrode is maintained is at or near ground potential.

Referring now to FIG. 8, one way of implementing an electrode drive circuit for each of the electrodes available for use in stimulation in a current management system will now be described. An electrode drive circuit 800 is provided for stimulation electrode $SE_1$ 110 having a current sink portion 804 and a current source portion 806. The current sink portion 804 is provided with a constant current reference $I_{REF1}$ 820 and the current source portion 804 is provided with a constant current reference $I_{REF2}$ 860. As explained above, when a given stimulation electrode $SE_1$ 110 through $SE_N$ 120 is being used in the course of a stimulation episode 600, the current sink portion 804 and the current source portion 806 cannot be operating at the same time.

Operation of the current sink portion 804 can be explained as follows: In this variation, the supply voltage $V_S$ 190 is a regulated supply that is referenced to ground and derived from a positive pin of a battery. Thus, the first constant reference current, $I_{REF1}$ 820 is substantially independent of voltage supply variations. The first constant reference current $I_{REF1}$ 820 flows through a first field effect transistor (nFET) M1 830 that is diode-connected. A second nFET transistor M2 840 is configured to mirror the current in the first transistor M1 830. The sources of the first and second nFET transistors M1 830 and M2 840 are at a potential corresponding to $V_{BOTTOMRAIL}$, which in one variation is a negative voltage $V_N$, e.g., −8.0 V). A first operational amplifier 850 modulates the gate of a third nFET transistor M3 858 so that the voltage at the drains of the first and second nFET transistors M1 830 and M2 840 are maintained as equal. That is, a first input 852 to the first operational amplifier 850 is the voltage at the drain of the first nFET transistor M1 830 and a second input 854 to the first operational amplifier 850 is the voltage at the drain of the second (mirror) nFET transistor M2 840. A first operational amplifier output 856 is input to the gate of the third nFET transistor M3 858, and the drain of the third transistor nFET M3 858 is connected to the first stimulation electrode $SE_1$ 110. Thus, as the voltage at the first stimulation electrode $SE_1$ 110 varies, the first operational amplifier 850 will modulate the gate of the third nFET transistor M3 858 so that the drain voltages of the first and second nFET transistors M1 830 and M2 840 are equal. This configuration will keep the current through the mirroring transistor, i.e., the second nFET transistor M2 840 constant over a wide range of voltages at the first stimulation electrode $SE_1$ 110.

Operation of the current source portion 806 is substantially similar to that of the current sink portion 804 as described above, although pFET transistors are used instead of nFET transistors. More specifically, the current passing through a fourth diode-connected pFET transistor M4 870 corresponds to a second reference current $I_{REF2}$ 860. A fifth pFET transistor M5 872 is configured to mirror the current in the fourth pFET transistor M4 870. The sources of the fourth and fifth pFET transistors M4 870 and M5 872 are tied to $V_{TOPRAIL}$ 520, which in one variation is a positive voltage $V_P$, such as +8 V. A second operational amplifier 880 modulates the gate of a sixth pFET transistor M6 888 so that the voltage at the drains of the fourth and fifth pFET transistors M4 870 and M5 872 are maintained as equal. That is, a first input 882 to the second operational amplifier 880 is the voltage at the drain of the first pFET transistor M4 870 and a second input 884 to the second operational amplifier 880 is the voltage at the drain of the second (mirror) pFET transistor M5 872. A second operational amplifier output 886 is input to the gate of the third pFET transistor M6 888, and the drain of the third pFET transistor M6 888 is connected to the first stimulation electrode $SE_1$ 110. Thus, as the voltage at the first stimulation electrode $SE_1$ 110 varies, the second operational amplifier 880 will modulate the gate of the third pFET transistor M6 888 so that the drain voltages of the first and second pFET transistors M4 870 and M5 872 are equal. This configuration will keep the current through the mirroring transistor, i.e., the second pFET transistor M5 872 constant over a wide range of voltages at the first stimulation electrode $SE_1$ 110.

It will be apparent to one with skill in the art that the current to be sourced or sunk by a stimulation electrode may be made programmable in a variety of different ways. For example, in one variation, the range of possible currents that can flow through either a current sink portion 804 or a current source portion 806 of an stimulation electrode drive circuit can be increased by implementing the mirror transistors (e.g., the second transistor M2 840 in current sink portion 804 of electrode drive circuit 800 in FIG. 8 and the fifth transistor M5 872 in current sink portion 806 of electrode drive circuit 800) with a number of discrete transistors connected in parallel to control the current gain of the relevant circuit portion. In other words, and again with reference to FIG. 8, if the mirror transistor M2 840 in the current sink portion 804 is the same size as the diode-connected first transistor M1 830, then the current sunk through the first stimulation electrode $SE_{1110}$ will be substantially equal to the first reference current $I_{REF1}$ 820. If the mirror transistor M2 840 is instead implemented with, for example, 100 transistors in parallel and each of these 100 transistors is the same size as the first diode-connected transistor M1 830, then the current through the first stimulation electrode will be 100 times the value of the first reference current $I_{REF1}$ 820.

In still other variations, the reference currents for the current sink and current source portions of an electrode drive circuit for a stimulation electrode are programmable between a range of values based on programming instructions processed by another part of a current management system 100 (or another part of a neurostimulation system in communication with a current management system 100). Since the current flowing into or out of the first stimulation electrode is proportional to one of the reference currents (e.g., to the first reference current $I_{REF1}$ 820 if the current sink portion 804 of an electrode drive circuit 800 is engaged, and to the second reference current $I_{REF2}$ 860 if the current source portion 806 of an electrode drive circuit 800 is engaged), then making the reference current programmable makes the current that is sunk or sourced through the stimulation electrode programmable.

In other variations of the current management system, features may be included to optimize power consumption. By way of one example, a feature is included one or more electrode drive circuits, such as the electrode drive circuit 800 shown in FIG. 8, that allows the operational amplifiers 850, 880 in each of the current sink portion 804 and the current source portion 806 to be selectively controlled by an enable signal, for example, an enable input. This would allow the current flow through the third transistor M3 858 and the sixth transistor M6 888 to be turned on and off via control logic that causes the enable signal to change (e.g., go high and low). Since minimizing power consumption in an implantable device is often important (e.g., to avoid prematurely draining a battery that supplies power for the implantable system), and the operational amplifiers require power to function, being able to turn off the operational amplifiers when they are not being used in sourcing or sinking current would be in the interest of power conservation.

In still other variations of the current management system, features may be included that beneficially can be included to limit the current that can flow through a stimulation electrode notwithstanding the programming instructions and/or increase the current that can be delivered through a stimulation electrode when the voltages supplying the stimulation electrode drive circuits are insufficient to source or sink the amount of current that corresponds to the programming instructions. For example, the current management system 100 can be configured to establish a "TILT" condition whenever the system is unable to source or sink the amount of current it is programmed to source or sink through a given stimulation electrode. The amount of current programmed to flow will exceed the amount of current that can be caused to flow through a stimulation electrode when the product of the resistance to current flow at the electrode (which may include the impedance of the lead in which the electrode is disposed) and the amount of current programmed to flow is greater than available voltage for stimulation ("stimulation reservoir voltage"). In the case of the current sink portion 804 of the electrode drive circuit 800 of FIG. 8, the stimulation reservoir voltage may be equivalent to the voltage $V_{BOTTOMRAIL}$ which in turn may be equal to a value $V_N$.

When a TILT condition occurs, it may be recognized as the condition when an operational amplifier in a given stimulation electrode drive circuit (e.g., the first operational amplifier 850 of the current sink portion 804 of the electrode drive circuit 800 of FIG. 8) goes to its most positive limit (i.e., its positive rail). One way of recognizing a TILT condition may be to configure a threshold detector so that it compares (e.g., with a comparator) the output of an operational amplifier in a current sink portion or a current source portion of a stimulation electrode drive circuit to a reference voltage.

Upon occurrence of a TILT, the current management system 100 can be configured, for example, to do any of the following: (1) prevent any current to flow notwithstanding the programmed instructions; (2) automatically downwardly adjust the amount of current that is programmed to be sunk or sourced to an amount that can be delivered given the existing stimulation reservoir voltage; or (3) automatically upwardly adjust the stimulation reservoir voltage (e.g., if the stimulation reservoir voltage at issue is $V_P$, increase its value about ground potential, and if the stimulation reservoir voltage at issue is $V_N$, increase its value below ground potential), so that the originally programmed amount of current can flow through the stimulation electrode.

With regard to option (3), above, it will be appreciated that adjusting the reservoir voltage so that it not substantially greater than necessary at any given time to deliver a programmed amount of current will contribute to the efficiency with which the implantable neurostimulator (see, e.g., neurostimulator 410 in FIG. 4) uses power. For example, in one variation, the two voltage rails $V_{TOPRAIL}$ 520 and $V_{BOTTOMRAIL}$ 522 between which a stimulation electrode drive circuit is configured to operate might be programmed at initial time $T_0$ to be +3 V and −3V, respectively, where the battery that supplies the neurostimulation system is a 3 V battery. If at a later time $T_1$ the stimulation reservoir voltage is insufficient to support the programmed amount of current through a stimulation electrode (e.g., a TILT condition occurs), then the current management system 100 can be configured to automatically upwardly adjust the relevant stimulation reservoir voltage (e.g., $V_{TOPRAIL}$ 520 or $V_{BOTTOMRAIL}$ 522) up to the minimum voltage value that will support the programmed current. The values of the relevant stimulation reservoir voltages can be automatically adjusted throughout the life of the implantable neurostimulator (see, e.g., neurostimulator 410 in FIG. 4) in order to maintain optimum efficiency for the stimulation output stage.

Figure 9:
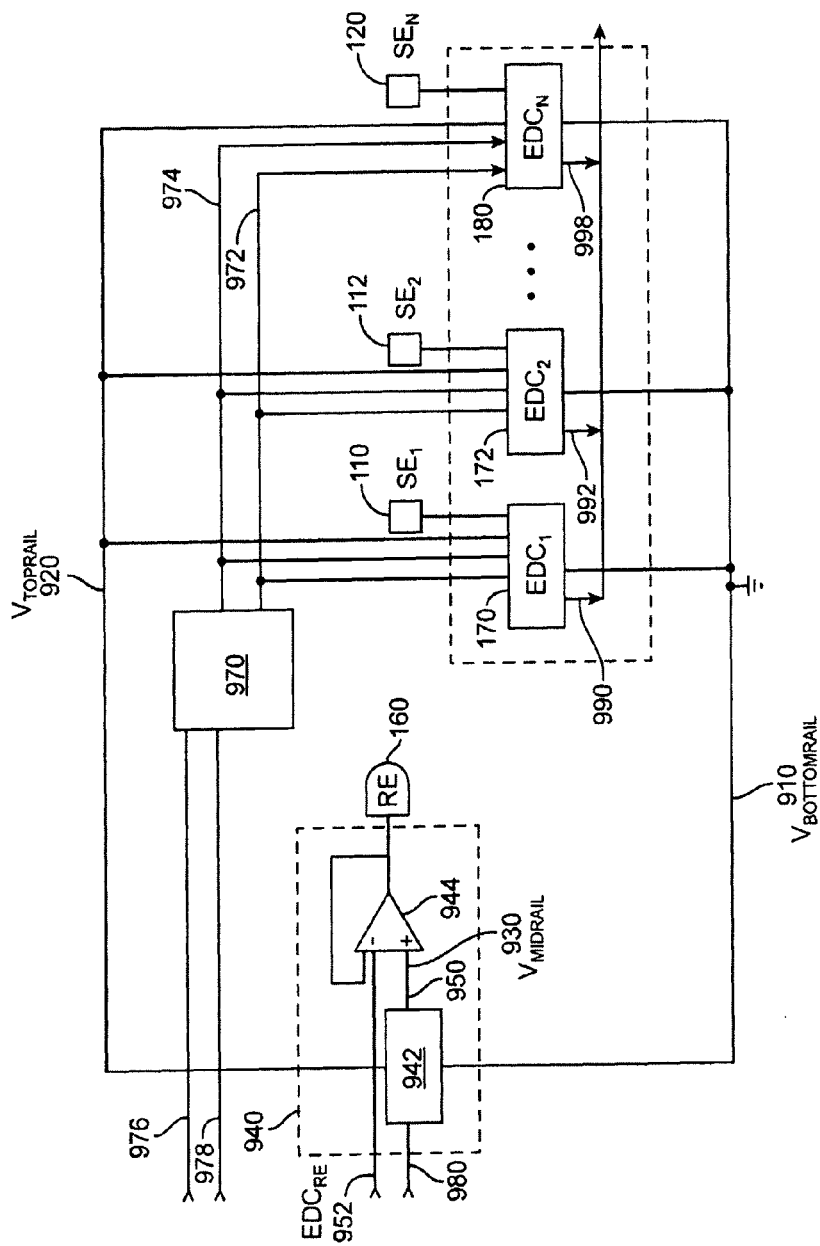
FIG. 9 is a schematic diagram of illustrating some of the circuit elements for a current management system for a stimulation output stage of a neurostimulation system where the potential at which the reference electrode is maintained at a voltage that is between ground and a positive voltage.

FIG. 9 is a schematic diagram of a variation of a current management system 100 for an implantable neurostimulator 12 in which the reference electrode RE 160 is maintained at a constant voltage in a range between ground and the positive voltage Vp (as contrasted with, for example, a current management system 100 that operates between positive and negative rails). In FIG. 9, the stimulation electrode drive circuits $EDC_1$ 170, $EDC_2$ 172 through $EDC_N$ 180 are configurable to sink or source current within the limits of stimulation reservoir voltages corresponding to a voltage $V_{BOTTOMRAIL}$ 910 and a voltage $V_{TOPRAIL}$ 920, and the reference electrode RE 160 is maintained at a constant potential $V_{MIDRAIL}$ 930 that is somewhere between the values of $V_{BOTTOMRAIL}$ 910 and $V_{TOPRAIL}$ 920. For example, an implantable neurostimulator (see, e.g., the neurostimulator 410 of FIG. 4) may have a power supply comprising a 3 V battery. One or more boost converters can be used to increase the voltage from the battery to create a $V_{TOPRAIL}$ 920=16 V and a $V_{BOTTOMRAIL}$ 910=0 V. The midrail voltage may be set at a point approximately half way between the two rails, or at $V_{MIDRAIL}$ 930=8 V. The current sink portions (not shown in FIG. 9) of the electrode drive circuits $EDC_1$ 170, $EDC_2$ 172 through $EDC_N$ 180 may be configured to operate between the boundaries of 0 V and +8 V, and the current source portions (also not shown in FIG. 9) of the electrode drive circuits $EDC_1$ 170, $EDC_2$ 172 through $EDC_N$ 180 may be configured to operate between the boundaries of +8 V and +16 V.

Referring still to FIG. 9, a current management system 100 may be provided with a reference electrode drive circuit $EDC_{RE}$ 940 which comprises a digital-to-analog converter (DAC) 942 and an reference electrode operational amplifier 944. Digital signal(s) 980 input to the DAC 942 determine a constant voltage signal (corresponding to or derived from a programmed value) from which the DAC 942 sets a top rail voltage $V_{TOPRAIL}$ 920 and a voltage reference 950. An enable signal 952 for the reference electrode operational amplifier 944 also is derived from a digital signal. The reference electrode operational amplifier 944 sets and maintains a selected voltage on the reference electrode 160 in response to the voltage reference 950 provided by the DAC 942 and the enable signal 952.

The DAC 942 also provides a voltage $V_{TOPRAIL}$ 920 that is the upper rail to a bias circuit 970. The bias circuit 970 receives digital control 976 and timing (e.g., clock) signals 978 as inputs (corresponding to programmed values) and produces an analog output 972 and a digital output 974. The analog output 972 corresponds to the information about the current for a particular sourcing or sinking segment of a stimulation episode for a particular stimulation electrode. The digital output 974 enables the corresponding stimulation electrode to perform its designated function. For example, the digital control input 976 and the timing input 978 to the bias circuit 970 may contain programmed instructions to select first stimulation electrode $SE_1$ 110 to source 1.5 mA at a first time period $T_1$ in a stimulation episode. The bias circuit 970 is configured to generate an analog signal 972 for the first stimulation electrode $SE_1$ 110 that establishes a reference current for the electrode of 1.5 mA. The digital output 974 comprises an enable signal for the first stimulation electrode $SE_1$ 110 so that, for example, the operational amplifier of the current source portion of the stimulation electrode drive circuit $EDC_1$ 170 is enabled to allow the 1.5 mA to flow through the first stimulation electrode $SE_1$ 110 for the first time period $T_1$.

Although in FIG. 9 only one bias circuit 970 is shown associated with the stimulation electrode drive circuits $EDC_1$ 170, $EDC_2$ 172 through $EDC_N$ 180, it will be appreciated that a dedicated bias circuit may be provided as a feature of each stimulation electrode drive circuit. Each bias circuit 970 would supply an analog signal 972 to its associated stimulation electrode drive circuit(s) $EDC_1$ 170, $EDC_2$ 172 through $EDC_N$ 180 as well as an enable signal 974.

Thus, it will be appreciated that the digital signals which control the operation of the stimulation electrode drive circuits (e.g., through one or more bias circuits) convey programmed instructions such as which function an electrode available for stimulation will perform at which time during a given stimulation episode (e.g., current source, current sink, high impedance or short circuit to ground), and what the amplitude of the current sourced or sunk by an electrode will be when it is configured to function as a source or sink. It further will be appreciated that the digital signals will have the effect of selecting which of the electrodes available for stimulation to use in a given stimulation episode. That is, the digital signal(s) enable the current sourcing portion of the electrode drive circuit $EDC_1$ 170 for stimulation electrode $SE_1$ at time $T_1$ to source 1 mA of current into the patient, then the stimulation electrode $SE_1$ 110 has thereby been selected for use in the stimulation episode, at least during time $T_1$.

With reference again to FIG. 9, each of the stimulation electrode drive circuits $EDC_2$ 172, $EDC_3$ 174 through $EDC_N$ 180 is configured to generate a signal representative of a TILT condition, i.e., TILT signal 990 for $EDC_1$ 170, TILT signal 992 for $EDC_2$ 172, and TILT signal 998 for $EDC_N$ 180, whenever the conditions prerequisite to a TILT condition for a given current sink portion or a current source portion for a stimulation electrode drive circuit exists.

It should be noted that as illustrated and described herein, each of the various components of the variations of the current management system 100 described is not necessarily a single physical or functional element that can be adequately represented in any illustration, and that physical or functional elements may be combined in various ways for the same or similar effect. For example, and not by way of limitation, a function described herein as being performed by hardware may be performed by software or a combination of software and hardware.

In some embodiments, the neurostimulation system (see, e.g., the neurostimulation system 400 of FIG. 4) with which the current management system 100 is used for a stimulation output stage in accordance with one or more of the foregoing variations can be used in combination with other types of systems for delivering stimulation to a patient. For example, the electrodes available for use in a stimulation episode that current flow through the electrodes could be disabled for current flow (for example, by programming the electrodes to go to a High Z state, and then the electrodes could be made available for use by another stimulation output stage, such as one that delivers voltage stimulation rather than current stimulation.

In still other embodiments, the neurostimulation system with which the current management system 100 is used for a stimulation output stage in accordance with one or more of the foregoing variations can be used in combination with a system that is configured to sense a physiological variable or variables from the patient. For example, one or more of the electrodes available for stimulation that are associated with a current management system 100 can alternatively be used to sense a signal from a patient, such as an electroencephalographic signal (or "EEG"). To accomplish this, the current management system 100 might be programmed to set the function of a stimulation electrode to high impedance, during which time the electrode can be used to sense a voltage differential, for example, in a field potential measurement to acquire an EEG signal. It will be apparent that in the context of a neurostimulation system that has both stimulation and sensing and/or signal detection and/or signal recording capabilities, the current management system 100 can be programmed so that some of the electrodes available for stimulation are used to source or sink current relative to the patient, and other of the electrodes available for stimulation can instead be configured for sensing and/or detection and/or recording during a stimulation episode or between stimulation episodes or both.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present invention without departing from the spirit and scope of the invention as it is defined in the appended claims.

I claim:

1. A stimulation output stage of a neurostimulation system that is at least partially implantable in a body of a human patient comprising:
    a plurality of stimulation electrodes implantable in the patient so that each is adjacent or in the patient's tissue;
    a plurality of stimulation electrode drive circuits, each of the stimulation drive circuits associated with one of the plurality of stimulation electrodes and including a current sink portion and a current source portion and having a voltage reservoir associated there with;
    a reference electrode;
    a reference electrode drive circuit associated with the reference electrode and having a constant reference voltage associated there with;
    a controller configured to output digital control and timing signals to a bias circuit, the bias circuit configured to provide a digital output and an analog output for each of a plurality of the stimulation drive circuits, the digital output corresponding to one of a plurality of program instructions that control an operation of the stimulation drive circuit to which the digital output is provided, and the analog output determining an amplitude of any current a stimulation electrode drive circuit will cause to be sourced or sunk through its associated stimulation electrode;
    wherein each of the plurality of stimulation electrode drive circuits is adapted to: in response to receipt of a first program instruction, enable the current source portion of the stimulation drive circuit to establish a reference current for the stimulation electrode associated with the stimulation drive circuit so that the stimulation electrode sources current into the patient; in response to receipt of a second program instruction, enable the current sink portion of the stimulation drive circuit to establish a reference current for the stimulation electrode associated with the stimulation drive circuit so that the stimulation electrode sinks current out of the patient; in response to receipt of a third program instruction, short the stimulation electrode associated with the stimulation drive circuit; and in response to receipt of a fourth program instruction, cause the stimulation electrode associated with the stimulation drive circuit to have a high impedance; and
    wherein the reference electrode drive circuit is adapted to maintain the reference electrode at a constant voltage so that the reference electrode sinks or sources current to balance the current being sourced or sunk by the stimulation electrodes.

2. The stimulation output stage of claim 1 wherein the reference electrode comprises an electrically conductive surface area of a housing for an implantable neurostimulator.

3. The stimulation output stage of claim 1 wherein the voltage reservoir is at a potential between ground potential and a positive voltage.

4. The stimulation output stage of claim 1 wherein the voltage reservoir is at a potential between a negative voltage and a positive voltage.

5. The stimulation output stage of claim 1 wherein each stimulation electrode drive circuit is configured to generate a signal corresponding to a condition that occurs when a voltage reservoir associated with a stimulation electrode drive circuit and a stimulation electrode is not sufficient to permit a programmed amount of current to be sourced or sunk through the stimulation electrode.

6. The stimulation output stage of claim 1 further comprising a feature that will automatically adjust the reservoir voltage within a predetermined range of voltages whenever the reservoir voltage is insufficient to allow a stimulation electrode drive circuit to source or sink a programmed amount of current through its associated stimulation electrode.

* * * * *